United States Patent [19]

Angelchik

[11] Patent Number: 4,991,594
[45] Date of Patent: Feb. 12, 1991

[54] METHOD AND APPARATUS FOR REMOVING ASCITIC FLUID FROM ABDOMINAL CAVITY

[76] Inventor: Jean P. Angelchik, 1728 W. Glendale Ave., Ste. 401, Phoenix, Ariz. 85021

[21] Appl. No.: 438,875

[22] Filed: Nov. 20, 1989

[51] Int. Cl.[5] .................. A61B 19/00; A61M 31/00
[52] U.S. Cl. .................................... 128/898; 604/8; 604/27; 604/49
[58] Field of Search ............... 128/898; 604/8, 27, 604/49

[56] References Cited

U.S. PATENT DOCUMENTS

| | | | |
|---|---|---|---|
| 3,540,451 | 11/1970 | Zeman | 604/27 |
| 3,910,283 | 10/1975 | LeVeen | 604/49 |
| 4,666,425 | 5/1987 | Fleming | 604/4 |

Primary Examiner—Alan Cannon
Assistant Examiner—Gary Jackson
Attorney, Agent, or Firm—Tod R. Nissle

[57] ABSTRACT

A method and apparatus for removing ascitic fluid from the peritoneal cavity. The method removes ascitic fluid through a free floating section of a patient's intestinal tract.

5 Claims, 2 Drawing Sheets

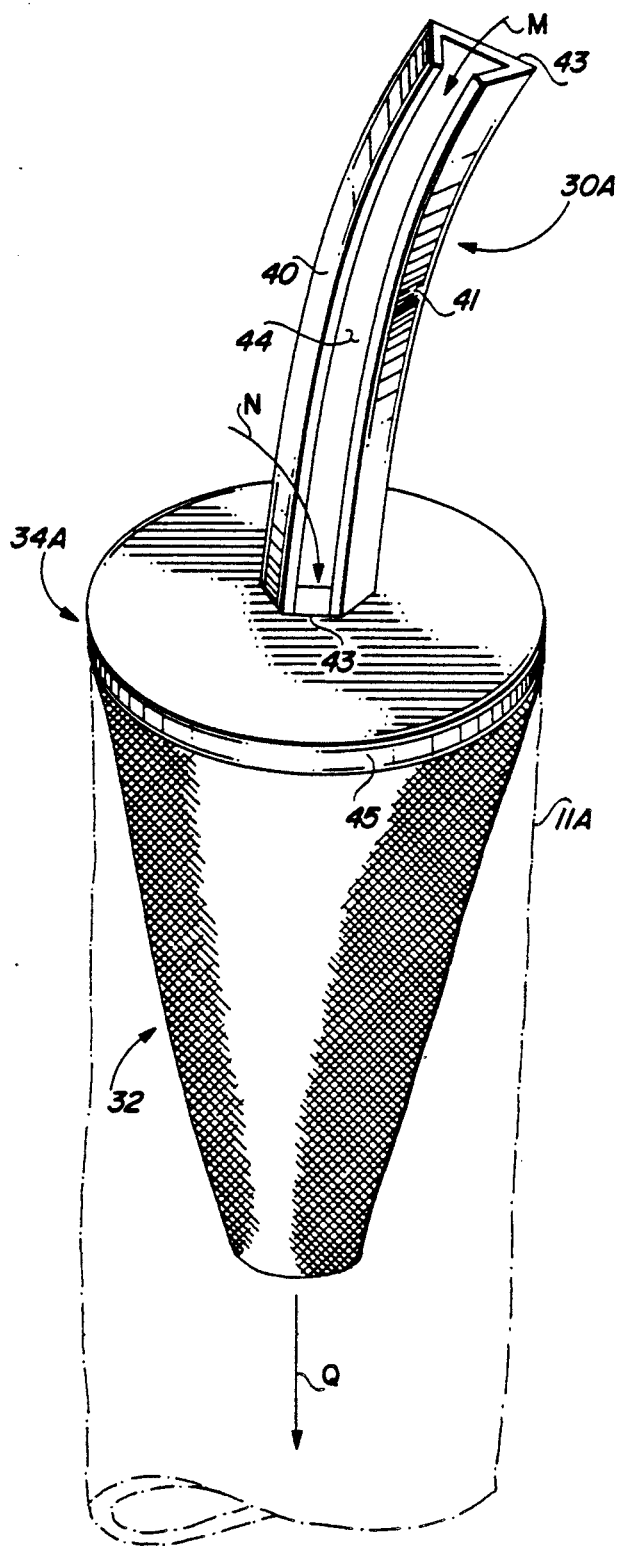
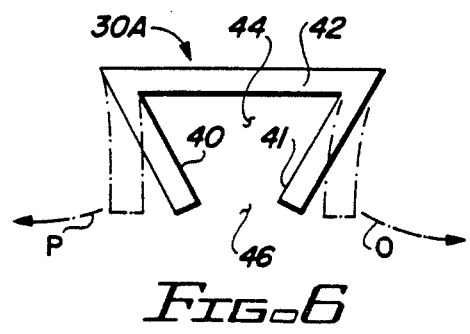
FIG. 5
FIG. 6

METHOD AND APPARATUS FOR REMOVING ASCITIC FLUID FROM ABDOMINAL CAVITY

This invention relates to a method for removing ascitic liquid from the peritoneal cavity of a patient.

More particularly, the invention relates to a method which removes ascitic liquid from the peritoneal cavity while minimizing the likelihood that infection in the ascitic fluid will be spread throughout the body, minimizing the likelihood that peritonitis will occur, and minimizing the likelihood that the heart and lungs will be overloaded and that an uncontrolled internal hemorrhage will occur in a patient.

Ascitis is a serious medical condition characterized by the accumulation of body fluid in the peritoneal cavity. The accumulation of ascitic fluid can, unless corrected, cause death. A common procedure for removing ascitic fluid from the peritoneal cavity is described in U.S. Pat. No. 3,910,283 to Leveen and basically comprises shunting the fluid into the large jugular vein or other large vein. Directing ascitic fluid into the jugular vein has important disadvantages. If there is a cancer in the ascitic fluid, directing the ascitic fluid into the jugular vein rapidly spreads the cancer throughout the body. In addition, the tube leading from the abdomen to the jugular vein can clog, requiring additional surgery. Finally, directing ascitic fluid into the veinous system tends to overload the heart and lungs and, in particular, to inhibit the clotting ability of the patient's blood. Directing ascitic fluid into the circulatory system can cause a patient to die from an uncontrollable hemorrhage.

Another method for removing ascitic fluid comprises utilizing a cannula which penetrates the abdominal cavity and has a drainage opening external of the body. See, for example, U. S. Pat. No. 3,540,451 to Zeman. A principal disadvantage of the Zeman apparatus is that infection can travel from outside the body, through the drainage opening and cannula into the abdominal cavity, causing peritonitis.

Accordingly, it would be highly desirable to provide an improved method for removing ascitic liquid from the peritoneal cavity, the improved method, in comparison to the prior art methods described above, reducing the likelihood that an uncontrollable hemorrhage will occur, that infection will be spread throughout the body, or that peritonitis will result.

Therefore, it is a principal object of the invention to provide an improved method for removing ascitic fluid from the abdominal cavity.

Another object of the invention is to provide an improved method which removes ascitic fluid from the peritoneal cavity without requiring that the fluid be shunted into the circulatory system or directed through a cannula extending from inside the abdominal cavity and through the abdominal wall to a drainage port external of the body.

A further object of the invention is to provide a method which removes ascitic fluid from the peritoneal cavity without requiring the utilization of a manually or mechanically operated fluid pumping system.

These and other, further and more specific objects and advantages of the invention will be apparent to those skilled in the art from the following detailed description thereof, taken in conjunction with the drawings, in which:

FIG. 5 is a perspective view illustrating another embodiment of the filter-valve used in the invention; and, FIG. 6 is a top view of the filter of FIG. 5 illustrating the mode of operation thereof.

Briefly, in accordance with my invention, I provide a improved method for removing ascitic liquid from the peritoneal cavity through the alimentary canal of a patient. The method comprises the steps of forming an opening in the wall of the intestine; severing the intestine at a selected point intermediate the opening and the stomach to form a pair of lengths of intestine comprising a first length having a first distal open end and extending from the distal end to the stomach, and a second length having a second distal open end and extending from the second distal end to the rectum, the opening being formed in the second length; attaching the first distal end to the opening such that food from the stomach passes through the first length of intestine, through the opening, and through a portion of the second length of intestine to the rectum; and, positioning the second distal open end in the peritoneal cavity, the intestine naturally suctioning ascitic fluid in the peritoneal cavity into the second distal end and through the second length of intestine toward the rectum.

In an alternate embodiment of the invention, I provide a method for removing ascitic fluid from the peritoneal cavity through the alimentary canal of a patient. The method includes the steps of forming an opening in the wall of the intestine; making a pair of incisions at spaced apart points along the intestine to resect a length of intestine, the length of intestine having first and second open ends, the remaining portion of the intestine having two segments, a first segment having a first distal open end and extending from the distal end to the stomach, and a second segment having a second distal open end and extending from the second distal end to the rectum; attaching the first distal end to the second distal end such that food from the stomach passes sequentially through the first and second segments to the rectum; attaching one end of the length of intestine to the opening; and, positioning the other end of the length of the intestine in the peritoneal cavity, the remaining portion of the intestine naturally suctioning ascitic fluid in the peritoneal cavity into the other end, through the length of intestine, through the opening, and toward the rectum through at least one of the pair consisting of the first and second segments.

In still another embodiment of my invention, I provide a method for removing ascitic liquid from the peritoneal cavity through the alimentary canal of a patient. The method comprises forming an opening in the wall of the intestine; and, attaching to the opening means for permitting ascitic fluid in the peritoneal cavity to flow into the opening under intestinal suction produced by peristalsis without permitting the contents of the intestine to escape from within the intestine, out the opening, and into the peritoneal cavity.

Figure 1:
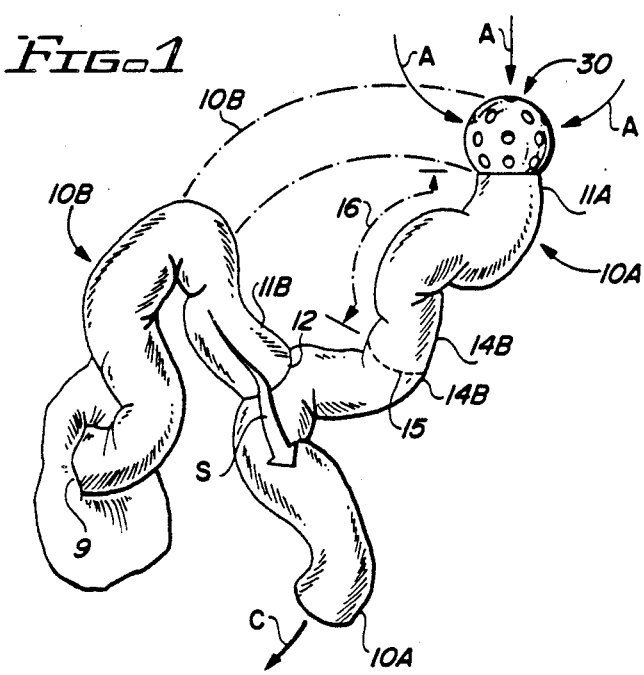
FIG. 1 is a perspective view of a portion of the alimentary tract of a patient illustrating the removal thereby of ascitic fluid from the peritoneal cavity.

Turning now to the drawings, which depict the presently preferred embodiments of the invention for the purpose of illustrating the practice thereof and not by way of limitation of the scope of the invention, and in which like reference characters refer to corresponding elements throughout the several views, FIG. 1 illustrates the small portion of the intestine of a human patient after an anastomosis has been performed in which the intestine is severed at a selected point to produce a first distal open end 11A and a second distal open end 11B. Open distal end 11B is sutured to an opening 12 formed in the wall of intestine 10A. Open free or floating end 11A is sutured to the filter-valve means 30 illustrated in FIGS. 2 and 3. In FIG. 1, the portion 10B of intestine includes and extends from distal end 11B through the ligament of Treitz 9 to the stomach of the patient. The portion 10A of the intestine includes and extends from distal end 11A to the rectum. Consequently, prior to severing the intestine to form open distal ends 11A and 11B, food from the patient's stomach passes along intestine portion 10B through the ligament of Treitz 9, past the point at which ends 11A and 11B were originally connected, through the intestine portion 10B past the point at which opening 12 is formed, and to the rectum. After the anastomosis is performed and the structure of the intestine is as shown in FIG. 1, food from the stomach passes through intestine 10B past the ligament of Treitz, through distal end 11B, through opening 12, and through intestine 10B in the direction of arrow C to the rectum of the patient. End 11B floats freely in the peritoneal cavity and is not sutured to an organ or any other part of the body. The length of intestine extending from opening 12 to end 11A also is not sutured to any part of the body. The free floating of end 11B is a significant feature of the invention because it permits the undulation of the length of intestine extending from opening 12 to end 11A. This undulation of the intestine in the peritoneal cavity facilitates absorption of fluid through end 11A into the intestine. Movement of member 30 tends to cause or force fluid to flow into or through openings 34, much like pulling a sponge through water causes water to flow into openings in the sponge. Undulation of the intestine also assists the peristaltic action of the intestine to move fluid along the intestine toward the rectum.

An alternate method for performing an anastomosis similar to that of FIG. 1 is to sever the intestine at two spaced apart points therealong and resect an auxiliary length, indicated by dashed arrows 16 in FIG. 1, of the intestine Auxiliary length 16 is formed by severing the intestine along dashed line 15 to form open ends 14A and 14B and by severing the intestine to form ends 11A and 11B. Immediately after the intestine is severed to form auxiliary length 16, portion 10B of the intestine extends up to end 11A in the manner indicated by dashed lines 10B in FIG. 1. The auxiliary length 16 of the intestine has first and second spaced apart open ends 11A and 14B (See FIG. 4). After resection of the auxiliary length 16 of intestine is completed, the remaining intestine has two remaining principal portions each with an open distal end 11B, 14A. One of the remaining principal portions of the intestine includes and extends from one of distal ends 11B to the stomach. The other of the remaining principal portions of the intestine includes and extends from the other distal end 14A to the rectum. The two open distal ends 11B and 14 formed during resection of the auxiliary length 16 of intestine are sutured to one another. After the two open distal ends 11B and 14A are sutured together food from the stomach travels along the intestinal tract past the point at which the two distal ends 11B and 14A are sutured together and then travels on to the rectum. After the two open distal ends 11B and 14A are sutured together, an opening 12 is formed in the wall of one of the remaining principal portions of the intestine. One end 14B of the auxiliary length 16 of intestine is sutured to opening 12. The other free floating end 11A of the auxiliary length 16 of intestine is positioned in the peritoneal cavity free of any sutures interconnecting to the human body either the end 11A or the auxiliary length of intestine extending out from opening 12 to end 11A. Ascitic fluid flows through open end 11A into the auxiliary length 16 of intestine and through the opening 12 formed in the wall of one of the remaining principal portions of the intestine to travel along the intestine toward the rectum. The open free end 11A of the auxiliary length 16 of the intestine can be provided with the filter-valve means of FIGS. 2 and 3.

In still another method for adapting the intestine in accordance with the principles of the invention, the intestine is not severed. Instead, an opening 12 is formed through the wall of the intestine at a selected site along the length of the intestine. One end of a synthetic conduit is sutured to opening 12. The other distal end of the conduit is positioned in the peritoneal cavity to draw ascitic fluid into said other distal end, through the conduit and into the intestine. The conduit can be fabricated from a silicone material or any other desired materials which will not adversely interact with the body of the patient. The distal end of the conduit can be attached to the filter-valve means of FIGS. 2 and 3.

Figure 2:
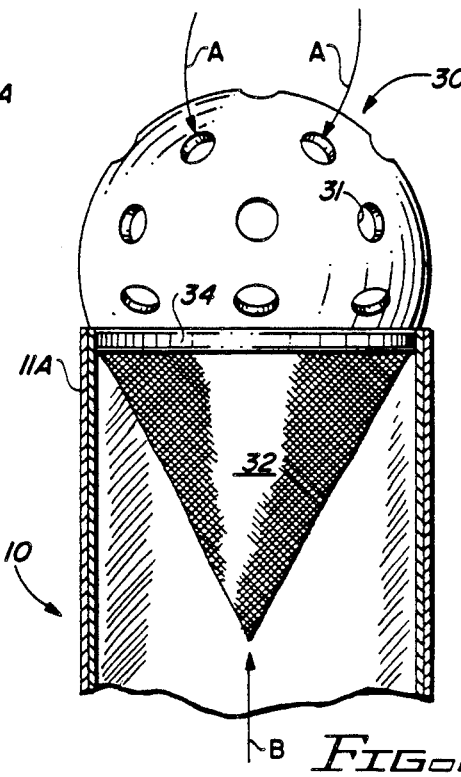
FIG. 2 is a partial perspective view of apparatus utilized in conjunction with the alimentary tract in FIG. 1.
Figure 3:
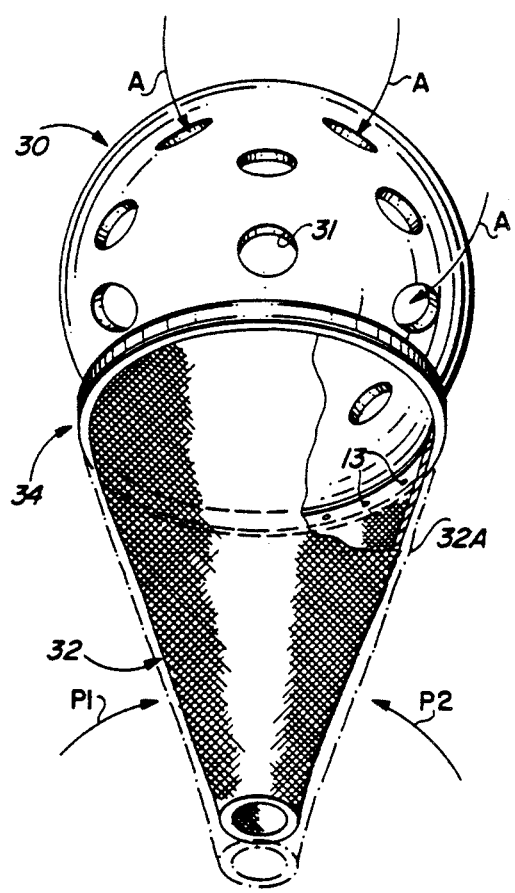
FIG. 3 is a lower front perspective view illustrating further construction details of the apparatus of FIG. 2.

The filter-valve means of FIG. 2 and 3 includes hollow spherical member 30. A plurality of spaced apart apertures 31 are formed through member 30. Both member 30 and conically shaped pliable valve member 32 are attached to a collar 34. Member 32 is attached to collar 34 at points 13 As depicted in FIGS. 1 and 2, distal end 11A of the intestine is sutured to collar 34 to affix the filter-valve means of FIG. 3 to distal end 11A. The open end 11A of the intestine can attract material which blocks or causes the end 11A of the intestine to heal. Spherical member 30 filters out such materials and generally permits only liquid to be drawn through apertures 31 and through open end 11A into the intestine. The shape and dimension of member 30 can vary as desired. Member 30 is preferably self cleaning so that it is unlikely that member 30 will become blocked and prevent the flow of ascitic fluid into the intestine. Member 30 can be fabricated from a silicone material or any other material which does not adversely react with the body of a patient.

Pliable valve member 32 functions to prevent the backflow of material from inside the intestine out through open end 11A into the peritoneal cavity. Conically shaped member 32 is formed of a fluid impermeable pliable, collapsible woven or non-woven piece of material. When fluid flows into member 30 and end 11A in the direction of arrows A in FIGS. 1, 2 and 3, valve member 32 permits the fluid to pass through opening 14 into the intestine. If, however, fluid attempts to backflow in the direction of arrow B in FIGS. 2 and 3, the valve member 32 collapses in the manner shown in FIG. 2 and blocks such backflow of liquid from the intestine into the peritoneal cavity. Accordingly, valve member 32 serves an important function in preventing material in the intestine from escaping into the peritoneal cavity.

Such material could infect the abdominal cavity and cause peritonitis.

The functioning of valve 32 is useful in conjunction with the undulation or compression and expansion of the intestine. When in FIG. 1 free end 11A moves, fluid can flow through openings 34 and valve 32 into the intestine. An undulation in or movement or resilient compression of the "free" length of intestine extending from end 11A to opening 12 can increase the pressure on fluid in the "free" length of intestine and cause fluid to flow back out through openings 34. Since valve 32 prevents fluid from flowing back out in the direction of arrow B through openings 34, the fluid is instead forced through opening 12 to move down the intestine in the direction of arrows S and C in FIG. 1. Accordingly, the combined functioning of valve 32 and the undulation or resilient compression of the "free" length of intestine simulates a pump. This "natural" pump provided by the combined functioning of the valve 32 and undulation of the "free" length of intestine is desirable because normal muscular contractions and movement of the internal body organs which occur during exercise or during ordinary day-to-day activities like eating meals, bathing, working, or shopping can compress and release the "free" length of intestine. The periodic compression of the "free" length of intestine by muscular contractions or internal organs facilitates operation of the "natural" pump comprising valve 32 and the "free" length of intestine. When the intestine is released after being compressed, a small suction or draw can be generated which helps move ascitic fluid through openings 34 into the intestine.

Various prior art teachings lead away from the invention. First, in the prior art the intestines are ordinarily attached to a selected point, either an organ or another intestine. Second, the suction produced by peristalsis of the intestine or the movement of chyme through the intestine can be relatively weak. Third, leaving the open end of a bowel in the peritoneal cavity is not advisable because the body uses its best efforts to close and heal the open end of the intestine. The free, floating natural pump of the invention remedies the problems and prejudices of the prior art.

Preferably, a tantalum filled silicone strip is attached to collar 34 such that after implantation of the valve--filter member, radiographic examination will reveal the position of collar 34 and the valve-filter member in the body. Radiopaque markers can be attached to member 30, valve 32, or at selected points along the intestine.

While valve 32 can take on any desired shape and dimension, the conically shaped valve of FIGS. 2 and 3 is preferred because it is normally open and is sensitive to small changes in pressure which occur from any point around the periphery of valve 32. An increase in pressure from the direction indicated by arrow P2 in FIG. 3 can cause valve 32 to close, as can an increase in pressure from the direction indicated by arrow P1, and as can an increase in pressure from any other direction(s) which inwardly displaces the conical wall of valve 32. The normally open state of valve 32 is desirable because it facilitates the flow of ascitic fluid into end 11A, i.e., the incoming fluid does not have to be under a pressure necessary to overcome a force inherent in the structure of the valve to force the valve to open.

A second valve, indicated by dashed lines 32A in FIG. 3, can be utilized in conjunction with valve 32. Valve 32A is attached to the outer portion of collar 34. Valve 32 is attached to the inner portion of collar 34, and there is a space between concentric valves 32 and 32A. Valve 32A houses and tends to protect valve 32. If valve 32A becomes brittle or damaged from use, valve 32 serves as a backup valve which continues to function properly.

The use of a double valve 32, 32A construction is especially important if the filter-valve of FIG. 3 is directly mounted in an opening 12 formed in the wall of the intestine. Directly mounting the filter-valve involves suturing collar 34 to opening 12 such that valves 32 and 32A extend into the intestine. When valves 32 and 32A extend into the intestine, chyme traveling through the intestine contacts, and over time can damage, valve 32A.

Figure 4:
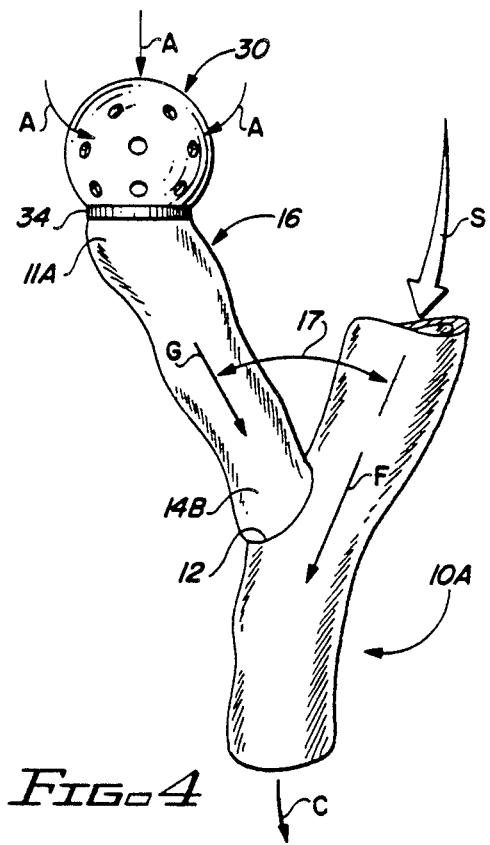
FIG. 4 is a perspective view of a portion of the alimentary tract of a patient illustrating the removal thereby of ascitic fluid from the peritoneal cavity.

It is preferred that the flow of ascitic fluid into the intestine readily merge with the normal flow of digested or partially digested food through the intestine. In FIG. 4, the auxiliary length 16 of intestine is sutured to opening 12 formed through the wall of portion 10A of the intestine. Digested or partially digested food from the patient s stomach flows into portion 10A in the direction indicated by arrow S and then flows from portion 10A along the intestinal tract toward the rectum in the direction indicated by arrow C. As the partially digested food moves by opening 12 it moves in the direction of arrow F. Ascitic fluid flows into member 30 in the direction of arrows A. Ascitic fluid flowing through the auxiliary length 16 of intestine flows in the general direction of arrow G into opening 12. It is preferred that the angle 17 between arrows G and F be less than 90°, normally 70° or less. This prevents food which is flowing through intestine 10A from traveling up into the auxiliary length 16 of intestine.

By way of example, the use of the method of my invention is illustrated with reference to FIGS. 1 to 3. My procedure consists of opening the abdominal cavity with an incision to expose the desired portion of the intestinal tract. While any portion of the intestine can be utilized, the jejunum and ileum of the small intestine are preferred. The small intestine can, through villi and lacteals, advantageously absorb body building protein and other materials found in ascitic fluid. In this example, it is assumed that the anastomosis is performed on the jejunum. The jejunum of the small intestine is severed to form a pair of opposed open distal ends 11A and 11B. An opening 12 is formed in portion 10A of the intestine. Distal end 11B is positioned adjacent and sutured to opening 12. The filter-valve means of FIG. 3 is affixed to distal end 11A by suturing end 11A to collar 34 in the manner illustrated in FIG. 2. Member 30 and end 11B are positioned in the peritoneal cavity to draw ascitic fluid into apertures 31 and through portion 10A of the intestine. The suction or draw naturally generated by the peristalsis of and action of the villi in the intestine 10A assists in drawing fluid through openings 30 into portion 10A of the intestine. If it is only intended that end 11A be utilized for a relatively short period of time to draw ascitic fluid into the intestine, the filter-valve means of FIG. 3 need not be attached to distal end 11A. In such circumstances, it may, however, still be desirable to insert a skeletal brace member in distal end 11A which extends intermediate the generally cylindrical wall of end 11A and functions to prevent the wall from collapsing or closing to seal end 11A.

An alternate filter-valve is illustrated in FIG. 5 and includes elongate filter member 30A, collar member 34A, and hollow valve 32 attached to member 34A. The distal end 11A of intestine is sealingly sutured to and extends around circular edge 45 of collar 34A. Filter 30A includes a pair of opposed, resilient flanges or flaps 40 and 41. Each flap 40, 41 is attached to elongate rectangular backing strip 42. Flaps 40, 41 and strip 42 partially encircle and define elongate channel 44. The lower end of member 30A is attached to member 34A and partially circumscribes an opening 43 formed through circular panel collar member 34A. As shown in FIG. 6, flaps 40 and 41 can resiliently move in the direction of arrows P and O to the positions indicated by ghost outlines 40A and 41A, respectively. After the forces acting on flaps 40 and 41 abate, flaps 40 and 41 can return to the normal operative position shown in solid outline FIG. 6. The opening 46 between the distal ends of flaps 40 and 41, along with the resilient pliable nature of the flaps, helps prevent channel 44 from being completely blocked so that liquid cannot flow into channel 44 in the manner indicated by arrows M and N in FIG. 5. Liquid flowing into channel 44 flows through opening 43, into valve 32, and out valve 32 in the direction indicated by arrow Q. If desired, a plurality of spaced apart apertures 43 can be formed through collar member 34A and a separate filter member 30A attached to each aperture in the manner that filter member 30A in FIG. 5 is attached to aperture 43.

Having described my invention in such terms as to enable those skilled in the art to understand and practise it, and having identified the presently preferred embodiments thereof, I claim:

1. A method for removing ascitic liquid from the peritoneal cavity through the alimentary canal, said method comprising:
   (a) forming an opening in the wall of the intestine;
   (b) attaching to said opening means for permitting ascitic fluid in the peritoneal cavity to flow into said opening without permitting the contents of said intestine to escape from within said intestine, out said opening, and into said peritoneal cavity.

2. A method for removing ascitis liquid from the peritoneal cavity through the alimentary canal, said method comprising:
   (a) forming an opening in the wall of the intestine;
   (b) making a pair of incisions at spaced apart points along the intestine to resect a length of intestine, said length of intestine removed during said resection having first and second open ends, the remaining portion of said intestine having two segments,
      (i) a first segment having a first distal open end and extending from said distal end to the stomach, and
      (ii) a second segment having a second distal open end and extending from said second distal end to the rectum,
   (c) attaching said first distal end to said second distal end such that food from said stomach passes sequentially through said first and second segments to said rectum;
   (d) attaching to said opening one end of said length of said intestine removed during said resection; and,
   (e) positioning the other end of said length of said intestine removed during said resection in said peritoneal cavity, peristalsis of said intestine naturally drawing ascitic fluid in said peritoneal cavity into said other end, through said removed length of intestine, through said opening, and toward said rectum through at least one of the pair consisting of said first and second segments.

3. The method of claim 2 including means attached to said length removed during said resection for preventing the contents of said removed length from leaking out of said other end into said peritoneal cavity.

4. A method for removing ascitis liquid from the peritoneal cavity through the alimentary canal, said method comprising:
   (a) forming an opening in the wall of the intestine;
   (b) severing said intestine at a selected point intermediate said opening and the stomach to form a pair of lengths if intestine comprising
      (i) a first length having a first distal open end and extending from said distal end to said stomach, and
      (ii) a second length having a second distal open end and extending from said second distal end to the rectum, said opening being formed in said second length;
   (c) attaching said first distal end to said opening such that food from the stomach passes through said first length of intestine, through said opening, and through a portion of said second length of intestine to said rectum; and,
   (d) positioning said second distal open end in said peritoneal cavity free of any sutures interconnecting said second distal end to the human body, said distal end moving in said peritoneal cavity to cause ascitic fluid to flow into said second distal end, peristalsis of said intestine naturally drawing ascitic fluid in said peritoneal cavity into said second distal end and through said second length of intestine toward said rectum.

5. The method of claim 4 including means connected to said second length for preventing the contents of said second length from leaking out of said second distal end into said peritoneal cavity.

* * * * *